(12) United States Patent
Kim

(10) Patent No.: US 10,456,512 B2
(45) Date of Patent: Oct. 29, 2019

(54) BABY PRODUCT STERILIZER INCLUDING BREAST PUMP

(71) Applicant: CIMILRE CO., LTD., Cheonan-si, Chungcheongnam-do (KR)

(72) Inventor: Sang Ha Kim, Cheonan-si (KR)

(73) Assignee: CIMILRE CO., LTD., Cheonan-si, Gyeonggi-do (KR)

( * ) Notice: Subject to any disclaimer, the term of this patent is extended or adjusted under 35 U.S.C. 154(b) by 0 days.

(21) Appl. No.: 15/768,011

(22) PCT Filed: Nov. 3, 2015

(86) PCT No.: PCT/KR2015/011668
§ 371 (c)(1),
(2) Date: Apr. 13, 2018

(87) PCT Pub. No.: WO2017/065339
PCT Pub. Date: Apr. 20, 2017

(65) Prior Publication Data
US 2018/0303984 A1    Oct. 25, 2018

(30) Foreign Application Priority Data
Oct. 13, 2015   (KR) .......................... 10-2015-0142688

(51) Int. Cl.
*A61L 2/10*     (2006.01)
*A61M 1/06*    (2006.01)

(52) U.S. Cl.
CPC .............. *A61M 1/062* (2014.02); *A61L 2/10* (2013.01); *A61M 1/06* (2013.01); *A61L 2202/14* (2013.01); *A61L 2202/16* (2013.01); *A61L 2202/23* (2013.01); *A61L 2202/24* (2013.01); *A61M 2205/502* (2013.01); *A61M 2209/10* (2013.01)

(58) Field of Classification Search
CPC .................................... A61L 2/10; A61M 1/06
See application file for complete search history.

(56) References Cited

U.S. PATENT DOCUMENTS

2006/0147339 A1*  7/2006  Hunter ...................... A61L 2/10
                                                              422/24
2015/0352605 A1* 12/2015  Tiwari ....................... A61L 2/02
                                                             134/105

FOREIGN PATENT DOCUMENTS

| KR | 20-0366440 Y1 | 11/2004 |
| KR | 20-0447932 Y1 | 3/2010 |
| KR | 10-1099799 B1 | 12/2011 |
| KR | 10-1430672 B1 | 8/2014 |
| KR | 10-1456441 B1 | 10/2014 |

OTHER PUBLICATIONS

International Search Report for PCT/KR2015/011668 dated Jul. 6, 2016 from Korean Intellectual Property Office.

* cited by examiner

*Primary Examiner* — Sean E Conley
(74) *Attorney, Agent, or Firm* — Revolution IP, PLLC

(57) ABSTRACT

A baby product sterilizer having a breast pump includes: a body having a cap disposed openably and closably on the front surface thereof and a plurality of ultraviolet lamps located at the inside thereof to sterilize and dry baby products accommodated therein; a cover located at outer surfaces of the body; and the breast pump disposed between the body and the cover in such a manner as to be controlled by a controller mounted on the cover.

9 Claims, 5 Drawing Sheets

BABY PRODUCT STERILIZER INCLUDING BREAST PUMP

TECHNICAL FIELD

The present invention relates to a baby product sterilizer having a breast pump, and more particularly, to a baby product sterilizer having a breast pump provided integrally therewith in the interior thereof, thereby making it easy to keep the breast pump therein and also making it convenient to use the breast pump.

BACKGROUND ART

Generally, babies have low immunity, and therefore, baby products such as nursing bottles, nursing nipples, pacifiers, dishes, teethers, and toys, should be always sterilized before used or after used.

So as to sterilize baby products like nursing bottles, particularly, they are put in boiling water for a given period of time and are then dried naturally. At this time, a person who performs the sterilization may get burned by the boiling water, thereby undesirably causing a safety problem, and after the baby products are taken out from the boiling water, water remaining on them has to be completely removed, thereby undesirably causing inconveniences in use. The boiling sterilization is the best longest method, but if pollutants, heavy metals or endocrine disruptors are contained in the boiling water or steam, other pollution may be generated.

Recently, dishes or baby products made of corn starch by means of injection, as eco-friendly products, have been developed, and in this case, accordingly, it is impossible to perform the boiling sterilization for them, thereby increasing needs for sterilizers.

On the other hand, a sterilizer, which generates steam to sterilize nursing bottles with the generated steam, has been proposed.

According to the sterilizer using the steam, however, water for generating the steam should be always refilled in the interior of the sterilizer before the sterilization, thereby undesirably causing many inconveniences in use.

So as to solve the above-mentioned problems, accordingly, an ultraviolet sterilizer has been developed. According to the conventional ultraviolet sterilizer, an ultraviolet lamp is located on top of a body of the sterilizer to increase sterilization effects, but open surfaces of nursing bottles are located to face upward to dry the water in the nursing bottles, so that a long period of time is needed to dry the water remaining in the nursing bottles and further the remaining water blocks the permeation of ultraviolet rays into the nursing bottles, thereby failing to provide perfect sterilization.

On the other hand, a breast pump is used to artificially express breast milk from the breast (hereinafter, referred to as milk feeding portion) or to keep the expressed milk therein and is classified into a manual type breast pump that expresses breast milk by compressing and pumping a pipette type vacuum pump and an electric breast pump having vacuum pumping means embedded therein. As interests in breast feeding have been increased, recently, the electric breast pump has been widely used for more convenience.

The breast pump and the sterilizer are generally used separately from each other, and after the breast pump is used, a wide inhaler and a silicone valve of the breast pump are washed, sterilized in the sterilizer, and then kept in a given place. As the breast pump and the sterilizer are provided separately from each other, however, their storage place is large, and further, as the breast pump has a weight of about 300 g to 1 kg, it is somewhat heavy to move.

DISCLOSURE

Technical Problem

Accordingly, the present invention has been made to solve the above-mentioned problems, and it is an object of the present invention to provide a baby product sterilizer having a breast pump that has the breast pump provided integrally with a body thereof to allow a traffic line between the breast pump and the sterilizer to be shortened, thereby easily keeping internal parts of the breast pump in the sterilizer after the breast pump has been used and also keeping the breast pump even in a narrow place of the sterilizer through the integral type sterilizer and breast pump.

It is another object of the present invention to provide a baby product sterilizer having a breast pump that has one or more ultraviolet lamps located on left and right side surfaces or a back surface of a body thereof to increase sterilization effects.

Technical Solution

To accomplish the above-mentioned objects, according to the present invention, there is provided a baby product sterilizer having a breast pump, the sterilizer including: a body having a cap disposed openably and closably on the front surface thereof and a plurality of ultraviolet lamps located at the inside thereof to sterilize and dry baby products accommodated therein; a cover located at outer surfaces of the body; and the breast pump disposed between the body and the cover in such a manner as to be controlled by a controller mounted on the cover.

According to the present invention, desirably, the body includes a breast pump storage recess formed on top thereof to locate the breast pump therein.

According to the present invention, desirably, the body includes: a plurality of shelves located at the inside thereof to put the baby products thereon; an inner circulator disposed on the back surface thereof to circulate air in the interior of the body; an exhauster located below the inner circulator to move the air in the interior of the body to the outside; and the ultraviolet lamps disposed therein to sterilize and dry the baby products put on the shelves.

According to the present invention, desirably, the ultraviolet lamps are located on the upper and lower portions of the left and right sides of the body.

According to the present invention, desirably, the ultraviolet lamps are located on the upper and lower portions of the back surface of the body.

According to the present invention, desirably, the cover is open on the front surface thereof in such a manner as to be slidably coupled to the back surface of the body, while a space is being formed between the cover and the body to induce flow of air therethrough, and the cover includes a controller mounting recess formed on one side of top thereof to insertedly mount the controller thereinto.

According to the present invention, desirably, the controller includes: sterilizer control buttons for controlling the ultraviolet lamps and a fan of the sterilizer to sterilize and dry the baby products; a plurality of breast pump control buttons for controlling the breast pump to perform conversion to a massage mode and a breast milk expressing mode and to control breast milk expressing speeds and pressures;

and an LCD screen adapted to allow control states of the sterilizer and the breast pump to be checked with the naked eye.

According to the present invention, desirably, the cover includes: a filter located on the back surface thereof to filter fine dust of air introduced from the outside; an air suction part penetratedly located into the inner circulator of the body to circulate the air introduced into the body and thus to remove the water remaining on the baby products; and the fan located below the air suction part in such a manner as to be connected to the exhauster of the body to discharge the air circulated at the inside of the body to the outside and thus to purify the internal air of the body.

According to the present invention, desirably, the breast pump includes a module mounted onto the breast pump storage recess formed on top of the body and an air hose coupled to the module through an air hose connector formed on the back surface of the cover, so that breast milk is expressed in the state where the sterilizer and the breast pump are connected integrally with each other.

Advantageous Effects

Under the above-mentioned configuration, the present invention has the following advantages.

According to the present invention, the baby product sterilizer having the breast pump has the breast pump provided integrally with top of the body thereof to allow a traffic line between the breast pump and the sterilizer to be shortened, thereby easily keeping internal parts of the breast pump in the sterilizer after the breast pump has been used and also keeping the breast pump even in a narrow place of the sterilizer through the integral type sterilizer and breast pump.

In addition, the baby product sterilizer having the breast pump according to the present invention has the plurality of ultraviolet lamps located in the body thereof to uniformly distribute the ultraviolet rays to the interior of the body, thereby increasing the sterilization effects for the baby products.

Moreover, the baby product sterilizer having the breast pump according to the present invention has the ultraviolet lamp located on the lower side of the body thereof to allow ultraviolet rays to be permeated into the interiors of vessels like nursing bottles having water collected therein, thereby enhancing drying effects in the vessels and increasing sterilization and disinfection effects through the ultraviolet rays.

EXPLANATIONS ON REFERENCE NUMERALS IN THE DRAWING

Figure 1:
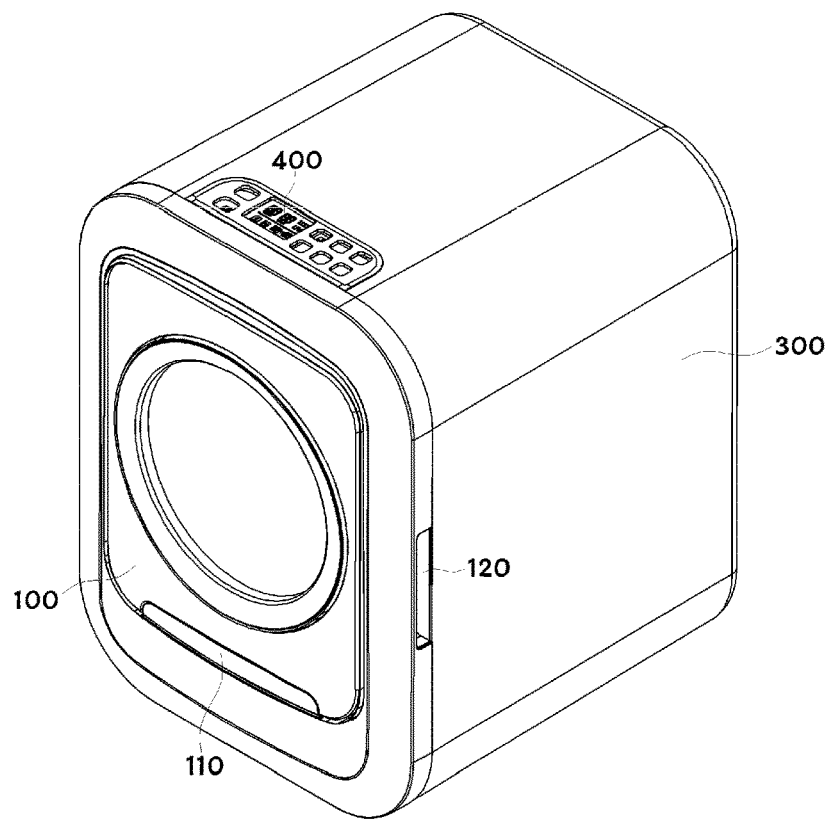
FIG. 1 is a perspective view showing a baby product sterilizer having a breast pump according to the present invention.

100: cover
110, 120: grasping groove
130: rubber packing coupling groove
140: check window
200: body
210: accommodation part
220: cap coupling part
230: rubber packing
240: breast pump storage recess
300: cover
310: controller mounting recess
320: filter
330: air suction part
340: fan
350: air hose connector
400: controller
410: PCB
420: button part
430: screen
500: breast pump
510: module
520: air hose
530: silicone valve
540: wide inhaler
550: silicone valve
560: nursing bottle

BEST MODE FOR INVENTION

Hereinafter, an explanation on a baby product sterilizer having a breast pump according to the present invention will be in detail given with reference to the attached drawing. In the description, it should be noted that the parts corresponding to those of the drawings are indicated by corresponding reference numerals. If it is determined that the detailed explanation on the well known technology related to the present invention makes the scope of the present invention not clear, the explanation will be avoided for the brevity of the description.

Figure 2:
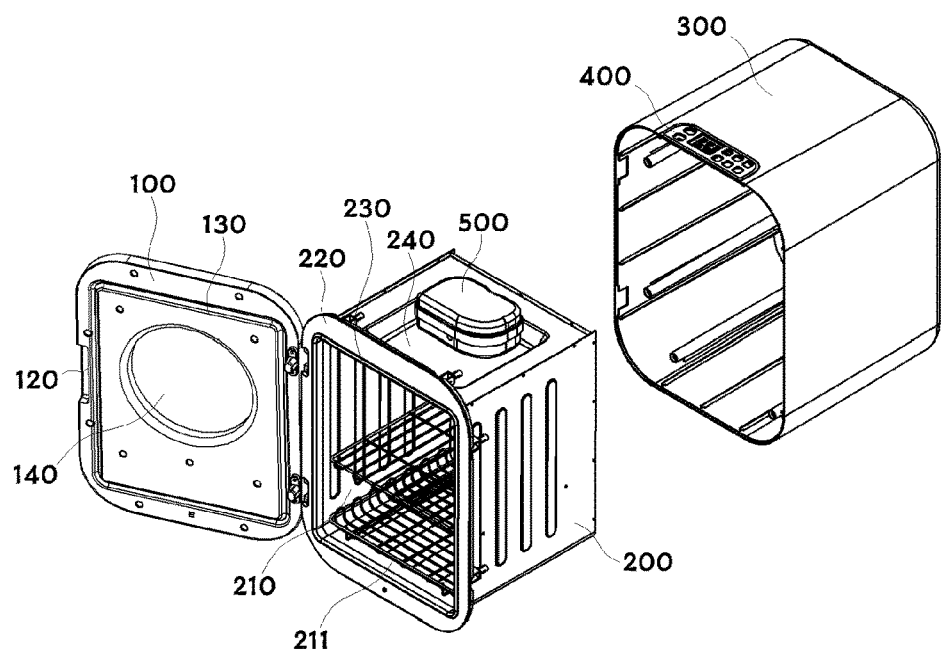
FIG. 2 is an exploded perspective view showing the baby product sterilizer having the breast pump according to the present invention.
Figure 3:
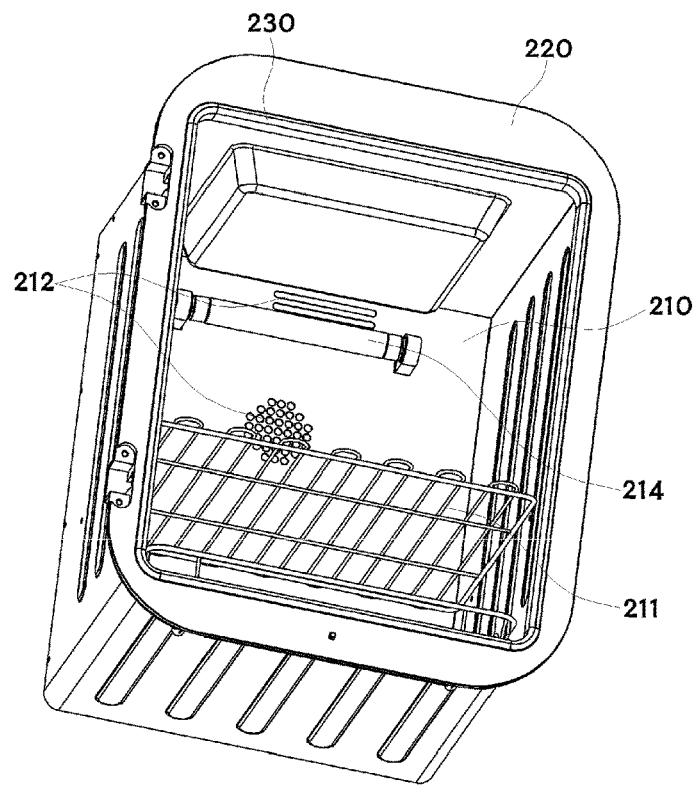
FIG. 3 is a bottom perspective view showing a body of the baby product sterilizer having the breast pump according to the present invention.
Figure 4:
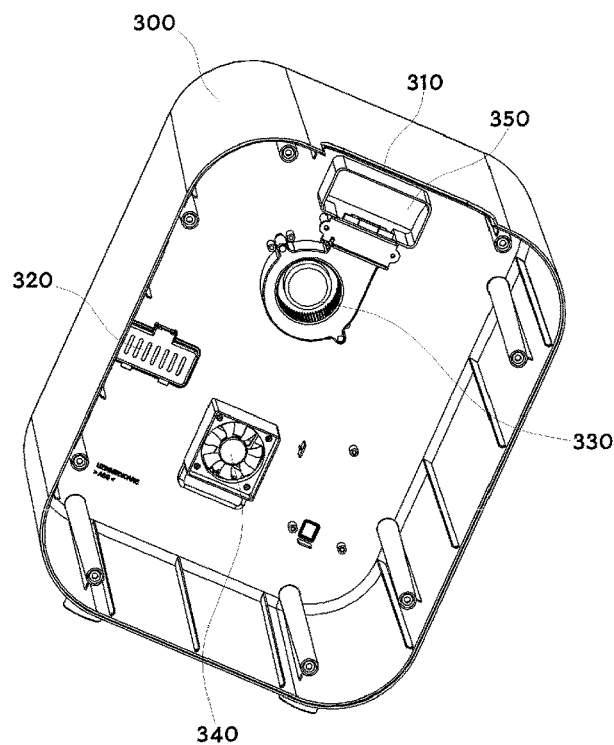
FIG. 4 is a perspective view showing a cover of the baby product sterilizer having the breast pump according to the present invention.
Figure 5:
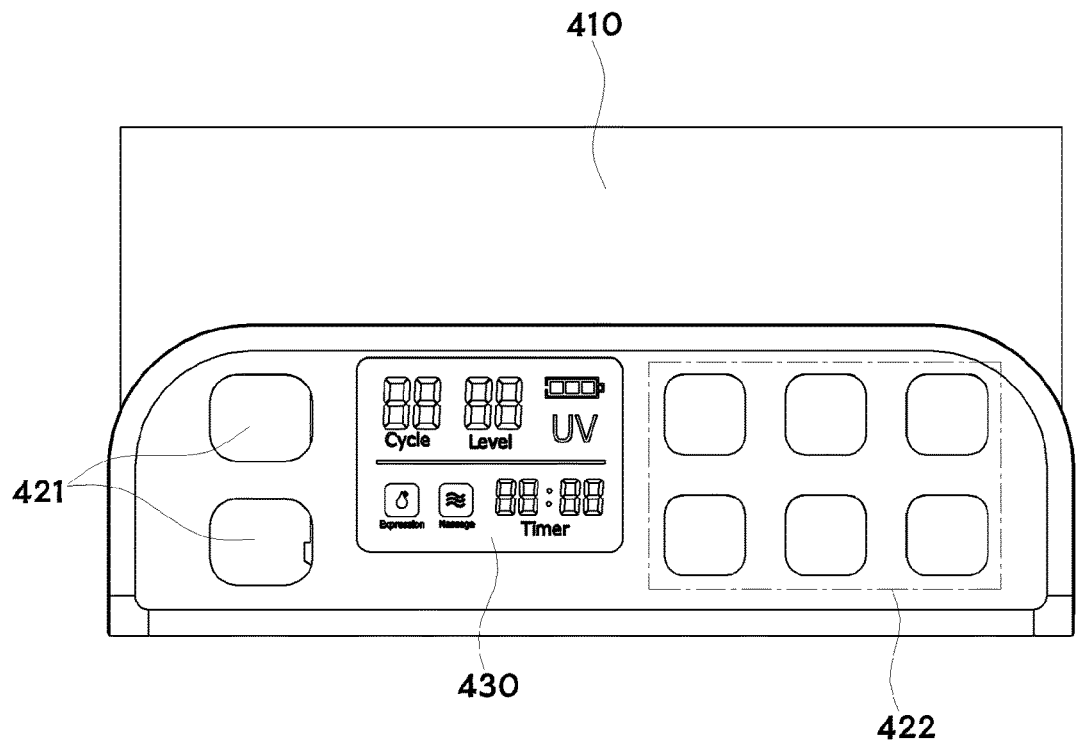
FIG. 5 is a top view showing a controller disposed on top of the cover of the baby product sterilizer having the breast pump according to the present invention.
Figure 6A:
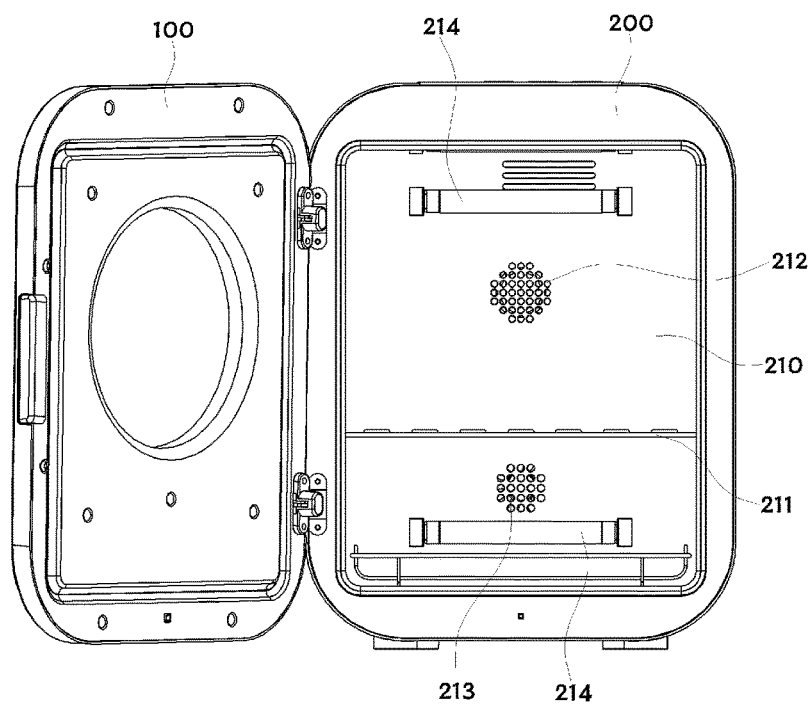
FIGS. 6A to 6C are front views showing states where ultraviolet lamps are disposed on the body of the baby product sterilizer having the breast pump according to the present invention.
Figure 6B:
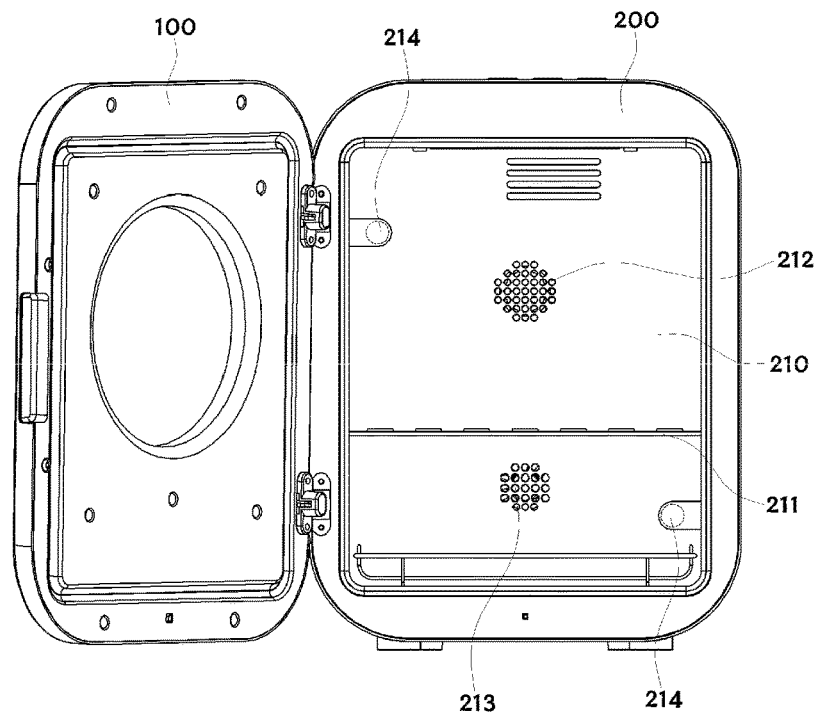
Figure 6C:
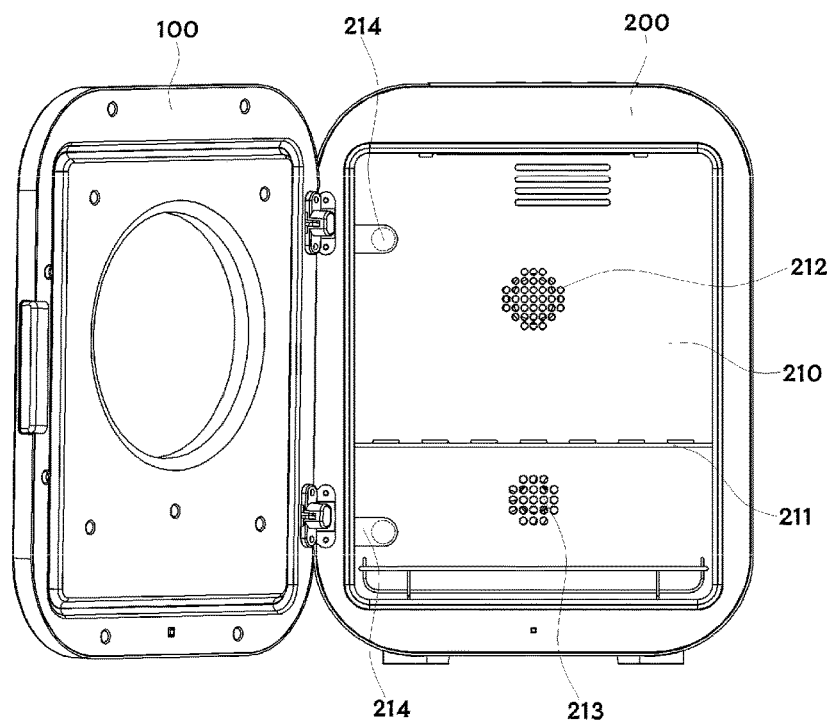
Figure 7:
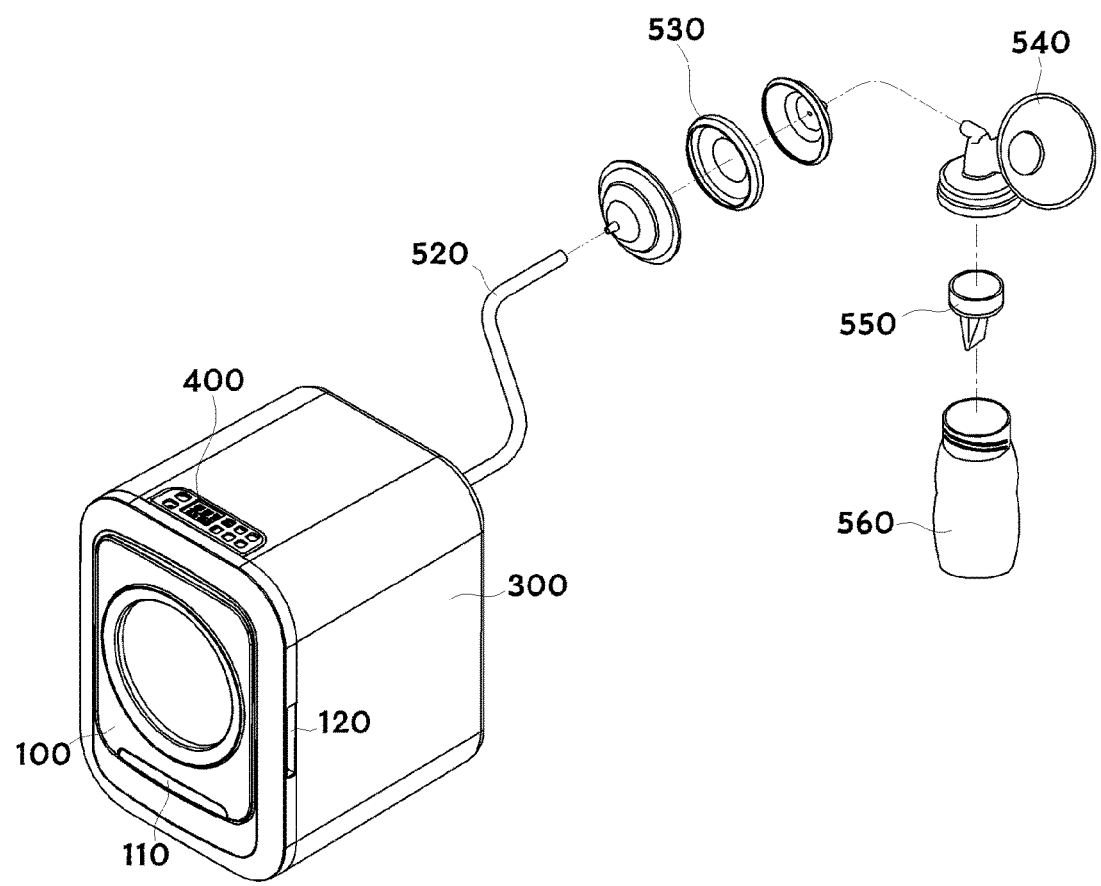
FIG. 7 is a perspective view showing the baby product sterilizer having a breast pump according to the present invention.

FIG. 1 is a perspective view showing a baby product sterilizer having a breast pump according to the present invention, FIG. 2 is an exploded perspective view showing the baby product sterilizer having the breast pump according to the present invention, FIG. 3 is a bottom perspective view showing a body of the baby product sterilizer having the breast pump according to the present invention, FIG. 4 is a perspective view showing a cover of the baby product sterilizer having the breast pump according to the present invention, FIG. 5 is a top view showing a controller disposed on top of the cover of the baby product sterilizer having the breast pump according to the present invention, FIGS. 6A to 6C are front views showing states where ultraviolet lamps are disposed on the body of the baby product sterilizer having the breast pump according to the present invention, and FIG. 7 is a perspective view showing the baby product sterilizer having a breast pump according to the present invention.

As shown in FIGS. 1 and 2, a baby product sterilizer having a breast pump according to the present invention includes a body 200 having a cap 100 disposed openably and closably on the front surface thereof, a cover 300 coupled slidably to the rear side of the body 200, and the breast pump 500 disposed between the body 200 and the cover 300.

The cap 100 is rotatable openably and closably to the body 200 and has grasping grooves 110 and 120 formed on a lower side surface and one side surface thereof to provide conveniences in use for a user and rubber packing coupling grooves 130 formed along locations distant by a given distance from the edges of the rear surface thereof in such a manner as to allow the interior of the body 200 to be sealedly closed when the cap 100 is coupled to the body 200.

Further, the cap 100 has a check window 140 disposed on the center of the front surface thereof to check baby products put in the interior of the body 200.

The body 200 having a front surface sealedly closed by the cap 100 is made of stainless steel so that sterilization and dry can be more efficiently performed and sanitary effects can be enhanced. The body 200 has a shape of a general rectangle in such a manner as to be open on the front surface thereof and includes an accommodation part 210 for locating the baby products at the inside thereof, a cap coupling part 220 extended outwardly from the front edges of the accommodation portion 210 in such a manner as to couplably come into contact with the cap 100, and a rubber packing 230 disposed between the front edges of the body 200 and the cap coupling portion 220 in such a manner as to be sealably coupled to the rubber packing coupling grooves 130.

Furthermore, the body 200 includes a breast pump storage recess 240 formed downwardly from top thereof to locate the breast pump 500 therein. The breast pump storage recess 240 has a shape of a general rectangle in such a manner as to be tapered inwardly, and accordingly, light emitted from an ultraviolet lamp 214 as will be discussed later is reflected on slant surfaces of the lower sides of the breast pump storage recess 240 and is thus distributed to the interior of the body 200.

Moreover, the body 200 has concave and convex patterns formed longitudinally on both side surfaces and underside thereof so that the ultraviolet rays generated from the ultraviolet lamp 214 are scatteredly reflected and are thus distributed to the interior of the body 200.

The accommodation part 210 has a plurality of shelves 211 located at the inside thereof to put the baby products thereon, an inner circulator 212 disposed on the back surface thereof to circulate air in the interior of the body 200, an exhauster 213 located below the inner circulator 212 on the back surface thereof to move the air in the interior of the body 200 to the outside, and the ultraviolet lamp 214 for drying and sterilizing the baby products put on the shelves 211.

The shelves 211 are mounted on protrusions (not shown) formed on both side surfaces of the accommodation part 210 and have shapes of meshes made of a heat resistant resin so that no hormone is detected from the shelves 211 by means of the heat emitted from the ultraviolet lamp 214. The shelves 211 are multi-staged to accommodate the baby products having various sizes, such as teethers, toys, nursing bottles, and dishes, therein according to the sizes of the baby products.

The inner circulator 212 introduces an external air introduced through an air suction part 330 located on the cover 300 as will be discussed later into the interior of the accommodation part 210, circulates the external air, removes the water remaining on the baby products, and thus makes it easy to permeate the ultraviolet rays into the baby products. At this time, the air suction part 330 has a filter adapted to filter fine dust in the air to prevent the fine dust from being attached to the baby products put in the accommodation part 210.

Further, the exhauster 213 is connected to a fan 340 located on the cover 300 as will be discussed later and thus moves the internal air to the outside to purify the internal air.

The ultraviolet lamp 214 is located on the back surface of the accommodation part 210, and otherwise, one or more ultraviolet lamps 214 are located on both side surfaces of the accommodation part 210. In detail, they are located on the upper and lower sides of the accommodation part 210 to evenly distribute the ultraviolet rays to the interior of the accommodation part 210 and to further increase the sterilization effects for the baby products located on the upper side thereof as well as the baby products located on the lower side thereof.

For example, as shown in FIGS. 6A to 6C, the ultraviolet lamps 214 are located on the upper and lower sides of the back surface of the accommodation part 210, alternately on the upper side of the left side surface of the accommodation part 210 and the lower side of the right side surface thereof, serially on the upper and lower sides of the left side surface of the accommodation part 210, or serially on upper and lower sides of the right side surface of the accommodation part 210. So as to prevent a quantity of power consumed from being increased, on the other hand, three or more ultraviolet lamps 214 are not disposed in the accommodation part 210.

The cover 300 is open on the front surface thereof in the same manner as the body 200 and has a shape of a general rectangle in such a manner as to be slidably coupled to the back surface of the body 200.

A space is formed between the cover 300 and the body 200 to induce flow of air therethrough, and the cover 300 has a controller mounting recess 310 formed on one side of top thereof to insertedly mount the controller 400 thereinto.

Further, the cover 300 includes a filter 320 located on the back surface to filter fine dust of air introduced from the outside, the air suction part 330 penetratedly located into the inner circulator 212 of the body 200 to circulate the air introduced into the body 200 and thus to remove the water remaining on the baby products, and the fan 340 located below the air suction part 330 in such a manner as to be connected to the exhauster 213 of the body 200 to discharge the air circulated at the inside of the body 200 to the outside and thus to purify the internal air of the body 200.

The controller 400 is located into the controller mounting recess 310 formed on top of the cover 300 and includes a PCB 410 located on underside thereof and a button part 420 and an LCD screen 430 located on top thereof to control the sterilizer and the breast pump.

The button part 420 includes sterilizer control buttons 421 for controlling the ultraviolet lamp and the fan of the sterilizer to sterilize and dry the baby products and a plurality of breast pump control buttons 422 for controlling the breast pump to perform conversion to a massage mode and a breast milk expressing mode and to control breast milk expressing speeds and pressures.

The sterilizer control buttons 421 turn on and off the fan 340 connected to the exhauster 213 and the ultraviolet lamp 214 as will be discussed later to perform drying and sterilization during a given period of time. The sterilizer control buttons 421 operate the fan 340 and the ultraviolet lamp 214 under an automatic course, or if necessary, they operate the fan 340 or the ultraviolet lamp 214, independently of each other. So as to sequentially perform drying and sterilization at a time, generally, the sterilizer control buttons 421 operate the fan 340 and the ultraviolet lamp 214 for 40 or 60 minutes so that the heater and the fan 340 operate at the same time to perform drying, and sterilization and ventilation are at the same time performed for final 10 minutes of the operating time of the sterilizer control buttons 421.

On the other hand, the ultraviolet lamp 214 always operates only for 10 minutes to exert the sterilization effects, and if the fan 340 is driven, it is driven under various courses, thereby removing smell from the interior of the sterilizer.

The breast pump control buttons 422 include a power button, a massage mode/breast milk expressing mode conversion button, breast milk expressing speed control buttons, and breast milk expressing pressure control buttons. The breast milk expressing pressure is divided into 1 to 12 levels, and the massage mode is divided into 1 to 5 levels, so that their levels are controlled using the corresponding + and − buttons according to a user's manipulation.

The control states through the sterilizer control buttons 421 and the breast pump control buttons 422 are displayed on the LCD screen 430 so that they can be checked with the naked eye.

The breast pump 500 is connected to the PCB 410 of the controller 400 and operates by means of the breast pump control buttons 422.

On the other hand, the breast pump 500 includes a module 510 mounted onto the breast pump storage recess 240 formed on top of the body 200, an air hose 520 coupled to the module 510 through an air hose connector 350 formed on the back surface of the cover 300, a silicone valve 530 and a wide inhaler 540 connected sequentially to one end of the air hose 520, a silicone valve 550 fitted to the underside of the wide inhaler 540, and a nursing bottle 560 coupled to the silicone valve 550, so that the breast milk can be expressed by the user.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

The invention claimed is:

1. A baby product sterilizer having a breast pump, the sterilizer comprising:
   a body having a plurality of ultraviolet lamps located at an inside of the body to sterilize and dry baby products accommodated in the inside of the body;
   a cap disposed on a front surface of the body;
   a cover located at outer surfaces of the body; and
   the breast pump disposed between the body and the cover in such a manner as to be controlled by a controller mounted on the cover.

2. The baby product sterilizer according to claim 1, wherein the body comprises a breast pump storage recess formed on a top surface of the body, wherein the breast pump is located in the breast pump storage recess.

3. The baby product sterilizer according to claim 1, wherein the body comprises:
   a plurality of shelves located at the inside of the body to put the baby products thereon;
   an inner circulator disposed on a back surface of the body to circulate air in the interior of the body;
   an exhauster located below the inner circulator to move the air in the interior of the body to the outside; and
   the ultraviolet lamps disposed therein to sterilize and dry the baby products put on the shelves.

4. The baby product sterilizer according to claim 3, wherein the ultraviolet lamps are located on the upper and lower portions of the left and right sides of the body.

5. The baby product sterilizer according to claim 3, wherein the ultraviolet lamps are located on the upper and lower portions of the back surface of the body.

6. The baby product sterilizer according to claim 1, wherein a front surface of the cover is open in such a manner as to be slidably coupled to a back surface of the body, while a space is being formed between the cover and the body to induce flow of air therethrough, and the cover comprises a controller mounting recess formed on one side of a top surface of the cover, wherein the controller is inserted into the controller mounting recess.

7. The baby product sterilizer according to claim 1, wherein the controller comprises:
   sterilizer control buttons for controlling the ultraviolet lamps and a fan of the sterilizer to sterilize and dry the baby products;
   a plurality of breast pump control buttons for controlling the breast pump to perform conversion to a massage mode and a breast milk expressing mode and to control breast milk expressing speeds and pressures; and
   an LCD screen adapted to allow control states of the sterilizer and the breast pump to be checked with the naked eye.

8. The baby product sterilizer according to claim 3, wherein the cover comprises:
   a filter located on a back surface of the cover to filter fine dust of air introduced from the outside;
   an air suction part penetratedly located into the inner circulator of the body to circulate the air introduced into the body and thus to remove water remaining on the baby products; and
   a fan located below the air suction part in such a manner as to be connected to the exhauster to discharge the air circulated at the inside of the body to the outside and thus to purify the internal air of the body.

9. The baby product sterilizer according to claim 2, wherein the breast pump comprises;
   a module mounted onto the breast pump storage recess; and
   an air hose coupled to the module through an air hose connector formed on a back surface of the cover.

* * * * *